United States Patent [19]

Frommer et al.

[11] Patent Number: 4,948,908
[45] Date of Patent: Aug. 14, 1990

[54] ORGANO PHOSPHORUS COMPOUNDS AND PESTICIDAL COMPOSITIONS

[75] Inventors: Moshe A. Frommer, Rehovot; Yoffi Segall, Ramat Hasharon; Ezra Shirin, Tel Aviv, all of Israel

[73] Assignee: Ramot Purotech, Ltd., Tel Aviv, Israel

[21] Appl. No.: 73,447

[22] Filed: Jul. 14, 1987

[30] Foreign Application Priority Data

Jul. 15, 1986 [IL] Israel ........................................ 79423

[51] Int. Cl.$^5$ ................................................ C07F 9/40
[52] U.S. Cl. ..................................... 558/193; 558/190
[58] Field of Search ................. 558/190, 193; 514/132

[56] References Cited

U.S. PATENT DOCUMENTS 4,233,434 11/1980 Kraus et al. .................... 210/500.38
4,360,480 11/1982 Kraus et al. .

Primary Examiner—Ferris H. Lander
Attorney, Agent, or Firm—Browdy & Neimark

[57] ABSTRACT

The invention relates to a new family of organophosphorus compounds. The compounds have a biological activity and can be used as insecticides. The compounds belong to the group of bis-aminophenyl phosphoric acid esters.

7 Claims, No Drawings

ORGANO PHOSPHORUS COMPOUNDS AND PESTICIDAL COMPOSITIONS

FIELD OF INVENTION

The invention relates to a family of organo phosphorus compounds which have a biological activity and which can be used, amongst others, as pesticides. The novel compounds are bis-amino-phenyl phosphoric acid esters, of the formulas given hereunder. There is also provided a process for the production of these. There are further provided pesticidal compositions which contain as active ingredient compounds of the present invention. Other and further features of the invention will become apparent hereinafter.

BACKGROUND OF THE INVENTION

Similar compounds are disclosed in Israel Patent No. 62916 which corresponds to U.S. Pat. No. 4,360,480. The present invention relates to a specific family of organo phosphorus compounds, which are not in the wide ambit of the compounds of the said patents.

SUMMARY OF THE INVENTION

According to the present invention there are provided novel organo phosphorus compounds. More specifically, there are provided novel bis-amino-phenyl phosphoric acid esters, a process for the production of these and biologically active compositions, and especially pesticidal compositions, which contain a compound of the present invention as active ingredient. More specifically, the compounds of the present invention are of the general formula

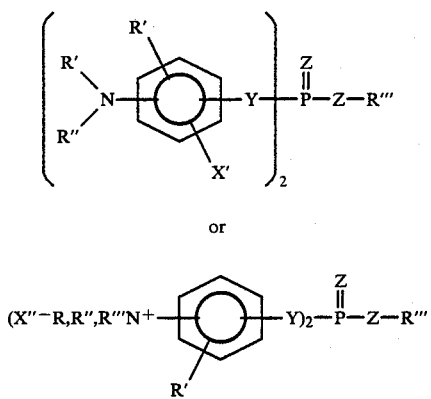

wherein:
  Z designate independently oxygen or sulfur:
  Y designates O, S, or N (R')
  R' designates —H or lower alkyl
  R" designates —H, lower alkyl, phenyl, —COR', —CONHR', —SO$_2$C$_6$H$_4$—CH$_3$;
  R''' designates H, Ar, —CH$_2$COOR', —CH$_2$CONHR', —CH=CHCOOR' or —CH=CH—CONHR', which aryl is optionally substituted by one or more alkyl, alkenyl, nitro, halo or cyano;
  X' and X" designate F, Cl, Br;
with the proviso that R' and R" are not simultaneously hydrogen, except for the compound of the formula

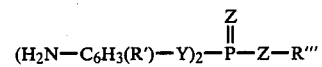

Compounds of general Formula I, above, wherein at least one of R', R" and R''' is hydrogen, are useful as ion exchange agents. Such compounds can be polymerized or copolymerized according to the process set out in Israel Patent No. 54646 or in U.S. Pat. No. 4,233,434 to form polymeric ion exchange resins which can be used for the extraction of metal ions, and especially of heavy metal ions such as uranium ions. Preferred compounds are those wherein Ar designates substituted aryl as above defined.

The term alkyl generally designates alkyl groups, which may be straight or branched and which contain up to 4 carbon atoms. Compounds of the present invention are effective biocides, and are especially useful as pesticides. They can be administered by conventional means of application in the form of sprays, as dusts etc, with conventional formulations of the type used for organo-phosphorus pesticides. The compounds of the invention can be used in the form of slow-release formulations of the type used in the home or in other closed spaces.

PREPARATION PROCEDURES

The novel compounds can be prepared according to one or more of the following general reaction schemes:
Scheme 1*
One mole of R'''—OH is reacted with one mole of

in the presence of a base (acid acceptor) to form the dihalide III.

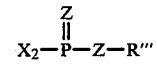

The dihalide (usually a chloride or a bromide) is treated with a nitroaromatic nucleophile of the general formula

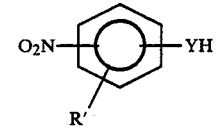

to yield reaction product IV

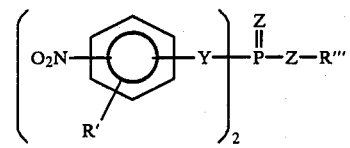

which dinitro compound is reduced chemically or by catalytic hydrogenation to form the corresponding diamine V:

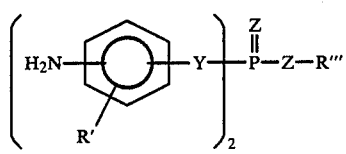
V which diamine V is treated with R'X, and with R"X to form compound I and afterwards R*X to form the quarternary ammonium salt II.

* Relevant for R'''≠CH=CH COOR', CH=CH CONHR', or Ar substituted by one or more nitro or cyano groups.

Scheme 2**

The dihalide 111 is reacted with the substituted amine VI

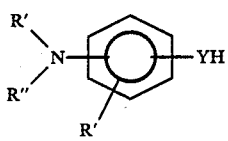
VI to form Compound 1.

** Relevant for any R''' but requires R'≠H if R" is a lower alkyl.

Scheme 3
One mole of

is reacted with two moles of the nitroaromatic nucleophile of the general formula

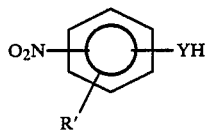

to form compound V11.

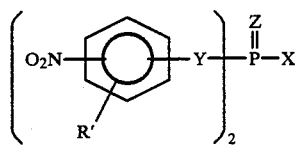
VII

If R''' is Ar, CH₂ COOR' or CH₂ CONHR' compound VII is reacted with R'''—ZH to form compound IV from which compounds I or II can be prepared as described above.

If R''' is C₆H₄ (NO₂)

Prior to hydrogeneration compound VII is "blocked" by a protective group by substituting the halide X with a "protected non reductive" group designated schematically "B". The "blocked" compound has the general formula VIII

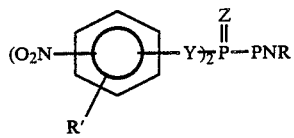
VIII

The "blocking" can be done by a variety of methods described in the literature (see e.g. J. F. W. McOme "Protective Groups in Organic Chemistry", Plenum Press, New York (1973).

It is possible to hydrolyse Compound VII to form the phosphoric acid

which is then esterified with e.g. EtI to form the phosphoric acid ethyl ester

Blocked Compound 1

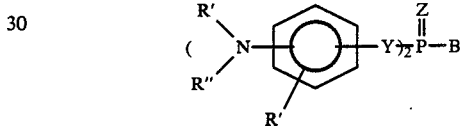

is then hydrolyzed with a base such as NaOH to form a sodium salt

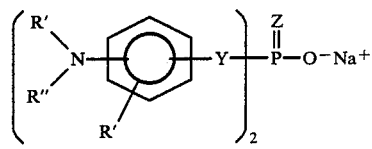

which is reacted with R'''X to form Compound 1.

Pesticidal Compositions containing compounds of Formula 1 or 11 include "the most important series of compounds from the point of view of practical crop protection—Enol Esters, Phenol Esters and Benzyl Esters" (see e.g. "The Chemistry of Organophosphorous Pesticides" by C. Fest and K. J. Schmidt, Springer-Verlag Berlin, Heidelberg, N.Y. 1973 pp 25, 29, 30 etc.)

The triesters covered by General formulas 1 or 11 contain the "acyl" moiety which according to Schraders' empirical rules must be possessed by biologically active phosphoric acid esters (ibid pp 40).

Due to the strong electro negative nature of R''' (e.g. the compositions containing compounds of the type

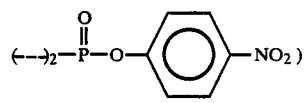

the compounds covered by General formulas 1 or 11 display a strong phosphorylating potential which according to Clark, Hutchinson, Kirby and Warren (ibid p 40, 41) is essential for insecticidal activity.

EXAMPLES

The invention is illustrated with reference to the following Examples, which are to be construed in a non-limitative manner.

EXAMPLE 1

Preparation of: phenyl bis-[4-N-acetamide-phenyl amido] phosphate also designated as: phosphoric acid phenyl ester-bis[4-N-acetamidephenyl-amide]:

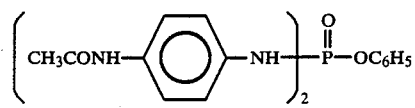
(IV)

Phenyl phosphate dichloride

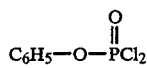
(X)

is obtained by heating under reflux for 12–15 hours of phenol with a slight excess of phosphorous oxychloride. The resulting phenyl phosphate dichloride is separated by vacuum distillation ; it is then condensed with 2 equivalents of p-nitroaniline in dry pyridine at 50° C. during 4–5 hours, precipitated with methanol and recrystallized from methanoldimethylacetamide to yield:

phenyl-bis[4-nitro-phenyl-amido]phosphate (also designated as phosphoric acid-phenyl ester-bis[4-nitro-phenyl-amide]) M.P.=300° C.

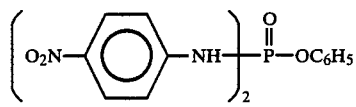
(XI)

The dinitro compound is hydrogenated at 4 atm over Pd/C to yield phenylbis[4-amino-phenyl amido]phosphate, (also designated as phosphoric acid-phenyl ester bis[4-amino-phenyl amide]),

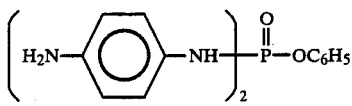
(XII)

Calculated: C=61.01%, H=5, 40% Found: C=61, 15%, H=5, 50% M.P.=191°-193° C.

The diamino compound (which gives a pronounced red colour reaction with TNBS-trinitrobenzene sulfonic acid) is dissolved in dioxane and reacted with equivalent amount of acetic anhydride.

A precipitate is formed within 10 minutes. The reaction mixture is left overnight at room temperature and evaporated to dryness. The material obtained is dissolved in methanol and precipitated with ether. The product obtained is the required diacetamide compound 1 as indicated by the facts that it gives a negative colour reaction with TNBS (trinitrobenzene sulfonic acid) and one spot of Rf=0.3 (as compared to Rf=0.4 of the starting material) on silicagel TLC; solvent being 7:1 methylene chloride:ethanol.

EXAMPLE 2

Preparation of phenyl-bis[4-N-acetamide phenyl]-phosphate, also designated as phosphoric acid-phenyl-ester-bis[4-N-acetamide-phenyl-ester]):

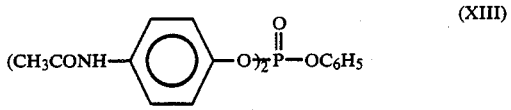
(XIII)

Phenyl phosphate dichloride obtained as described in Example 1 is treated at 60° C. during 18 hours with an excess of p-nitrophenol to yield: phenyl-bis[4-nitro phenyl]phosphate, also known as phosphoric acid-phenyl-ester-bis[4-nitro phenyl ester],

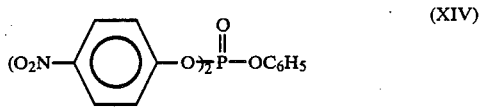
(XIV)

The product is precipitated in an HCl-ice mixture, filtered off dried at 60° C., and recrystallized from ethanol-water (M.P.=111°–112° C.) The dinitro compound is hydrogenated at 4 atm. over Pd/C to yield a compound V: phenyl-bis[4-amino-phenyl]-phosphate, also known as phosphoric acid phenyl-ester-bis[4-amino-phenyl-ester]) M.P.=128°–129° C. (V),

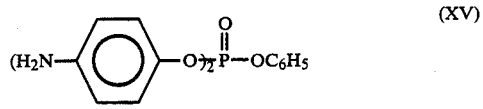
(XV)

The diamino compound (which gives a pronounced red colour reaction with TNBS—trinitrobenzene sulfonic acid) is dissolved in dioxane and equivalent amount of acetic anhydride is added. The reaction mixture is left overnight at room temperature and evaporated to dryness. The oily residue gives a negative colour reaction with TNBS, and one spot in silica-gel TLC (solvent methylene chloride-ethanol 7:1) Rf=0.55 (as compared to Rf=0.65 of the starting diamino compound indicating that it is the desired di-N-acetamide compound 1.

EXAMPLE 3

Preparation of Phenyl bis[4-NNN-trimethyl-ammonium-iodide-phenylamido]Phosphate, also designated phosphoric-acid-phenyl-ester-bis[4-NNN-trimethyl-ammonium-iodide-phenyl-amide]

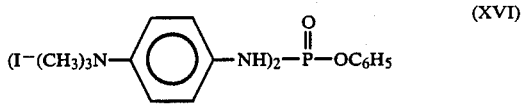
(XVI)

The diamine V (Example 1) is dissolved in a mixture of 4:1 acetone:0.5MNaHCO₃, and reacted overnight with excess MeI, methyliodide, at room temperature. The reaction mixture is then evaporated, dissolved in water and washed with ethyl acetate to remove impurities. The aqueous phase is then evaporated to dryness and the residue is washed several times with acetone to remove Sodiumiodide obtained as a by-product. The compound obtained is highly hygroscopic. The quarternary ammonium salt is very soluble in water but not in ethanol or acetone. It gives a negative reaction with TNBS.

Titration of compound 1 with Hg (ClO4)2 gives an equivalent weight of 353 which corresponds to a molecular weight of 706 as compared to a theoretical molecular weight of 694.

EXAMPLE 4

Preparation of: Phenyl-bis-[4-NNN-trimethyl-ammonium-iodide-phenyl]Phosphate, also designated phosphoric-acid-phenyl-ester-bis[4-NNN-trimethyl-ammonium-iodide-phenyl-ester]

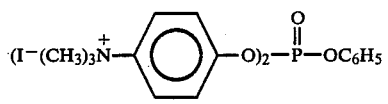
(II)

The diamino compound V (Example 2) is dissolved in a mixture of 4:1 acetone:0.5M NaH CO3, and reacted overnight at room temperature with excess MeI.

The following illustrates the preparation of some intermediates which are of use in the Examples 1 to 4. Examples 7 to 9 illustrate preferred compounds of the invention. The following are preferred compounds of the invention:

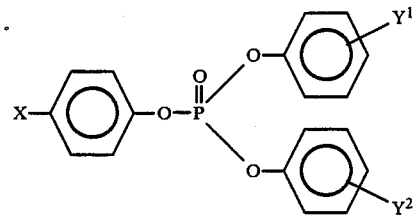

wherein
X is selected from —H and —NO2,
Y1 and Y2 are independently selected from m-N(CH3)2, m-N(CH3)3 and

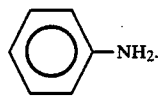

Specifically preferred compounds are those wherein X is —NO2 and both Y1 and Y2 are dimethylamine; where X is —NO2, Y1 is dimethylamine and Y2 is trimethylamine; and where X is —H, Y1 and Y2 are both

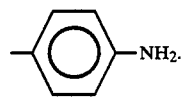

The following examples illustrate the invention by way of illustration with reference to some representative examples, illustrating the biological activity of compounds of the invention.

EXAMPLE 5

Compound XVII

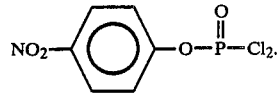

Phosphoric acid—(4-nitro-phenylester)-dichloride:

A quantity of 41 g. finely powdered, water free, sodium 4-nitro-phenolate is introduced, during 1 hour into 250 ml phosphorous oxychloride cooled with an ice-/sodium chloride mixture. After the end of the reaction the precipitated sodium chloride is filtered off, and the excess phosphorous oxychloride is removed under the reduced pressure. The residue is maintained during 1 hour at a pressure of 0.01 torr and distilled off: B.P.=128° C., M.P.=43.5°–44.5° C. The yield is 45%. Distillation is to be effected cautiously as the product is apt to decompose violently under other conditions of distillation.

Another procedure for the preparation of

Phosphoric acid—(4-nitro-phenyl ester)-dichloride is:

0.5 g. sodium chloride is added to 20.9 g. 4-nitro-phenol and 83 ml of freshly distilled phosphorus oxychloride, and the mixture is heated vigorously. The course of the reaction can be followed titrimetrically by absorbing of the evolved hydrogen chloride. After the end of the evolution of hydrogen chloride the excess of the phosphorus oxychloride is distilled off, under slightly reduced pressure. The residue (37.9 g) boils at 154°–155° C., yield being 33.8 g (88% of theory).

EXAMPLE 6

Compound XVIII

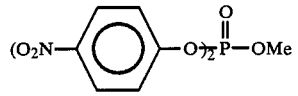

Phosphoric acid-methyl ester-bis-(4-nitrophenyl ester)

A solution of 1 g phosphoric acid-bis-(4-nitro-phenyl ester) in 8 ml warm anhydrous dioxan is cooled rapidly to room temperature, and then, 330 mg of bis-(4-methylphenyl)-carbodimide, are added immediately, whereupon immediate precipitation of bis-(4-methylphenyl) urea takes place. The reaction mixture is left to stand for 10 minutes and then, 0.063 ml of anhydrous methanol is added. The reaction mixture is maintained overnight in a dessiccator. The bis-(4-methylphenyl) urea is distilled off and washed with small quantities of dioxane. The combined filtrate is evaporated to yield a syrupy substance which is taken up in 10 ml chloroform and washed with water until neutral. By acidification with concentrated hydrochloric acid there is obtained from the solution 475 mg of phosphoric acid-bis-(4-nitro-phenyl ester). The chloroform solution is evaporated, and the residue is redistilled from aqueous ethanol yielding 490 mg (90%: M.P.=142°–143° C.)

EXAMPLE 7

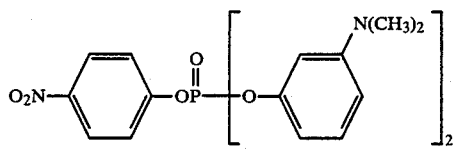

The apparatus used in this reaction comprised a three necked flask equipped with a mechanical stirrer, thermometer, ice water bath and a dropping funnel. A mixture of dry triethylamine (111.1 gr, 1 mole+10% excess), 3-dimethylaminophenol (150.7 gr, 1 mole+10% excess) and 700 ml dry ether was stirred in the reaction flask. A solution of 4-nitrophenylphosporyl chloride (129 gr, 0.5 mole) in 150 ml dry ether was added dropwise maintaining a gentle reflux during the addition. After stirring for 30 mins at room temperature, the solution was filtered, washed three times with water, dried ($Na_2SO_4$) and the solvent removed in vacuum. Drying at 90° C. for 4 hours gave 111 gr pure 1, M.P.=116°-117° C.

NMR δ $^{31}P$ ($CHCl_3$), −19 ppm (upfield of 85% $H_3PO_4$).

MS m/e 457 (M+).

EXAMPLE 8

(CH₃I analog)

A solution of 10 gr of 1 and 170 gr $CH_3I$ in 450 ml dry acetone was stirred for 48 hours at Room Temperature. At that period of time the reaction was completed as monitored by $^{31}P$ NMR. Trituration of the oil precipitate with methanol yielded 12 gr of a yellowish solid, M.P. 137°-140° C.

NMR δ $^{31}P$ −19.8 ppm ($CH_3OH$)
−19.2 ppm (DMSO)

Recrystalization from methanol gave 6.3 gr of pure product M.P. 147°-148° C.

MS(FAB), m/e 476 (M+$\overline{1}$|+).

EXAMPLE 9

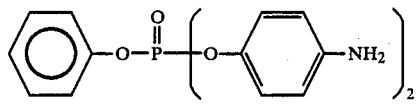

A. To 4-Nitrophenol (92 gr, 0.66 mole) in 1.5 liter dry $CH_2Cl_2$ were added phenyldichlorophosphate (73.2 gr, 0.33 mole of 95%). While stirred at room temperature, triethylamine (60 gr, 0.66 mole) was added dropwise and the solution stirred for addition 30'. Water (0.5 liter) was then added, the organic layer dried ($Na_2SO_4$) boiled 5' with charcoal, filtered and the solvent removed. After trituration with $CH_3OH$, 121.4 gr. of yellow solid was left, M.P. 11°-112° C.

δ $^{31}P$ - 19.4 ppm ($CH_2Cl_2$).

B. bis-4-nitrophenyl phenylphosphate (50 gr) from (A) was dispersed in $CH_3OH$ (500 ml) and reduced in a Paar (55 lbs pressure of $H_2$) with 10% Pd on charcoal (0.8 gr) for 2 hours at room temperature. On reaction termination the product dissolved in $CH_3OH$. Partial crystallizations from methanol gave 36.5 gr of bis-4-anilino phenylphosphate, M.P. 129°-130° C.

δ $^{31}P$ ($CH_3OH$) - 16.0. ppm.

MS, m/e 356 (100%, M+).

The anticholinestrerase activity of Example 8 was determined by observing changes in eel AcChE activity in the presence of 0.1-0.05 mM of the substrates (phosphate buffer, pH 7.0, 25° C.)

The Compound of Examples displayed a reversible mode of inhibition. Thus at an inhibition concentration of $5.5 \times 10^{-5}M$ at pH 7 in phosphate buffer, with eel AcChE, the activity of the enzyme is reduced to 85% within 30 seconds.

I claim:

1. An organo phosphorus compound of the formula

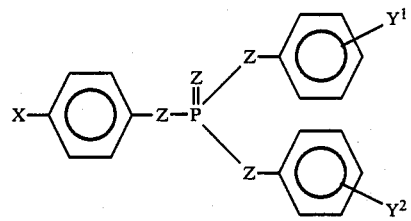

wherein X is hydrogen or —$NO_2$; $Y^1$ and $Y^2$ are independently selected from m-N(CH₃)₂, m-N(CH₃)₃ and $C_6H_4$—$NH_2$, and Z is independently selected from oxygen and sulfur.

2. A compound according to claim 1 wherein X is —$NO_2$ and both $Y^1$ and $Y^2$ are dimethylamine.

3. A compound according to claim 1 wherein X is —$NO_2$, $Y^1$ is dimethylamine and $Y^2$ is trimethylamine.

4. A compound according to claim 1 wherein X is hydrogen and $Y^1$ and $Y^2$ are both —$C_6H_4$—$NH_2$.

5. A compound according to claim 1 of the formula

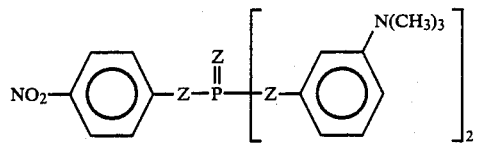

6. A compound according to claim 1 of the formula

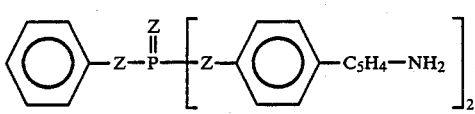

7. A pesticidal composition comprising a carrier and as active ingredient a pesticidally effective quantity of a compound claimed in claim 1.

* * * * *